(12) United States Patent
Nose et al.

(10) Patent No.: US 9,079,820 B2
(45) Date of Patent: Jul. 14, 2015

(54) PROCESS FOR PREPARING CHLORINE-CONTAINING FLUOROCARBON COMPOUND

(71) Applicant: DAIKIN INDUSTRIES, LTD., Osaka (JP)

(72) Inventors: Masatoshi Nose, Osaka (JP); Tsuneo Yamashita, Osaka (JP); Atsushi Maruo, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/289,947

(22) Filed: May 29, 2014

(65) Prior Publication Data
US 2014/0275654 A1    Sep. 18, 2014

Related U.S. Application Data

(63) Continuation of application No. 13/319,564, filed as application No. PCT/JP2010/058396 on May 12, 2010, now Pat. No. 8,779,219.

(60) Provisional application No. 61/213,164, filed on May 13, 2009.

(51) Int. Cl.
*C07C 17/087* (2006.01)
*C07C 17/35* (2006.01)
*C07C 17/20* (2006.01)

(52) U.S. Cl.
CPC .............. *C07C 17/35* (2013.01); *C07C 17/206* (2013.01)

(58) Field of Classification Search
CPC .............................. C07C 19/10; C07C 17/206
USPC .................................................. 570/164, 170
See application file for complete search history.

(56) References Cited

U.S. PATENT DOCUMENTS

| 2,787,646 | A | 4/1957 | Haszeldine et al. |
| 2009/0030247 | A1 | 1/2009 | Johnson et al. |
| 2009/0267022 | A1* | 10/2009 | Nappa et al. ............ 252/182.12 |

FOREIGN PATENT DOCUMENTS

| GB | 772484 | 9/1957 | |
| WO | 2007/079431 | 7/2007 | |
| WO | 2008/054781 | 5/2008 | |
| WO | 2009/003084 | 12/2008 | |
| WO | 2009/003157 | 12/2008 | |
| WO | WO2009/003084 A1 * | 12/2008 | ............ C07C 17/00 |
| WO | 2009/015317 | 1/2009 | |
| WO | 2009/018561 | 2/2009 | |
| WO | 2010/123148 | 10/2010 | |

OTHER PUBLICATIONS

International Search Report issued Apr. 27, 2011 in International (PCT) Application No. PCT/JP2010/058396.
A. N. Nesmeyanov et al., "Preparation of Some Fluoro Chloro Derivatives From 1,1,1,3-tetrachloropropane", Institute of Hetroorganic Compounds, Academy of Science of the USSR, Translated from Izvestiya Akademii Nauk SSSR, Otdelenie Khimicheskikh Nauk, No. 3, Mar. 1960, pp. 447-451, with CAPLUS Abstract XP-002603442.
E. T. McBee, "Fluorinated Derivatives of Propane", Journal of the American Chemical Society, No. 69, pp. 944-947, 1947.
R. N. Haszeldine, "Fluoro-olefins. Part II. Synthesis and Reactions of Some 3:3:3-Trihalogenopropenes", Journal of the Chemical Society, 1953, pp. 3371-3378.
Office Action dated Dec. 20, 2012 in European Patent Application No. 10725520.0.

* cited by examiner

*Primary Examiner* — Sudhakar Katakam
*Assistant Examiner* — Pancham Bakshi
(74) *Attorney, Agent, or Firm* — Wenderoth, Lind & Ponack, L.L.P.

(57) ABSTRACT

The present invention provides a process for preparing at least one chlorine-containing fluorocarbon compound selected from the group consisting of chlorine-containing fluoropropane compounds represented by Formula (1): $CF_nCl_{3-n}CHClCH_2Cl$, wherein n is 1 or 2, and chlorine-containing fluoropropene compounds represented by Formula (2): $CF_nCl_{3-n}CCl=CH_2$, wherein n is 1 or 2, wherein the process includes the step of contacting at least one chlorine-containing compound selected from the group consisting of 1,1,1,2,3-pentachloropropane, 1,1,2,3-tetrachloropropene, and 2,3,3,3-tetrachloropropene with hydrogen fluoride in the absence of a catalyst while heating. According to the present invention, the chlorine-containing propane and propene compounds having 1 or 2 fluorine atoms can be prepared by an industrially applicable, simple and effective process.

3 Claims, 1 Drawing Sheet

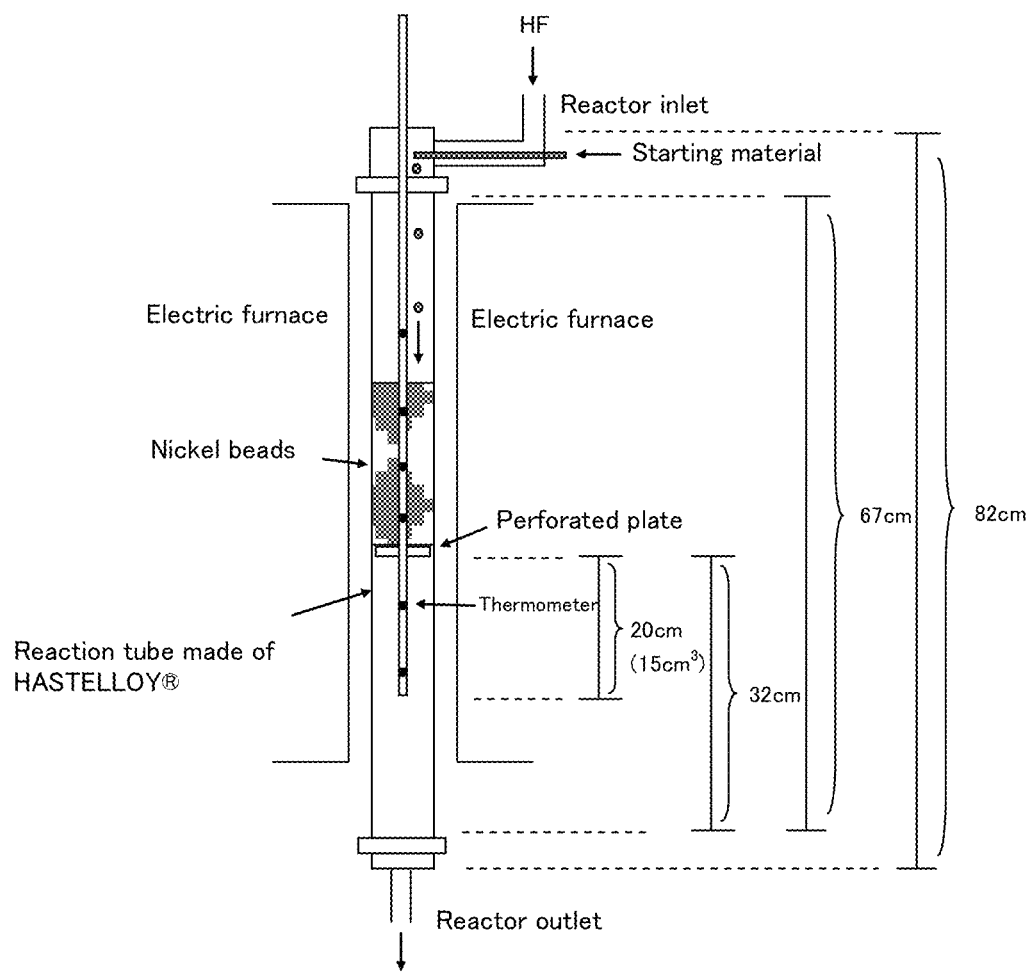

PROCESS FOR PREPARING CHLORINE-CONTAINING FLUOROCARBON COMPOUND

TECHNICAL FIELD

The present invention relates to a process for preparing fluorine- and chlorine-containing propane and propene compounds, which contain 1 or 2 fluorine atoms.

BACKGROUND ART

Chlorine-containing propane or propene compounds having 1 or 2 fluorine atoms, such as a chlorine-containing monofluoro or difluoro propane compound represented by Formula (1): $CF_nCl_{3-n}CHClCH_2Cl$, wherein n is 1 or 2, and chlorine-containing monofluoro or difluoro propene compounds represented by Formula (2): $CF_nCl_{3-n}CCl=CH_2$, wherein n is 1 or 2, are useful as an intermediate for manufacturing various fluorocarbons and also as various kinds of functional materials. In particular, 2,3-dichloro-3,3-difluoropropene (HCFC-1232xf) represented by $CF_2ClCCl=CH_2$ is a promising candidate for use as a cleaning agent, dry-cleaning solvent, and resist-removing agent.

Among the compounds represented by Formula (1) or (2) described above, it is known that 1,1,2,3-tetrachloro-1-fluoropropane (HCFC-241db, bp. 157° C.) represented by $CFCl_2CHClCH_2Cl$, and 1,2,3-trichloro-1,1-difluoropropane (HCFC-242dc, bp. 113° C. to 114° C.) represented by $CF_2ClCHClCH_2Cl$ can be prepared by fluorinating 1,1,1,2,3-tetrachloropropane (HCC-240db) (see Non-Patent Literature 1). However, because this method uses $SbF_3$ and $SbCl_5$ as the fluorinating agent, it poses a problem with regard to waste treatment upon disposal. Furthermore, in this method, the yield of HCFC-241db is only about 18%, and the yield of HCFC-242dc is only about 28%; therefore, a higher yield is desired.

As an alternative, a method is known wherein $CF_2ClCH=CH_2$ (HCFC-1242zf) or $CF_2ClCHClCH_3$ (HCFC-252dc) is used as a starting material and the starting material is chlorinated using chlorine. However, this method has drawbacks, including the fact that the starting material is not readily available, handling the chlorine is difficult, and the selectivity is low (see Patent Literature 1 and Non-Patent Literature 2).

An example of a known process for preparing 2,3,3-trichloro-3-fluoropropene (HCFC-1231xf, bp. 98.5° C. to 99° C.) represented by $CFCl_2CCl=CH_2$, and 2,3-dichloro-3,3-difluoropropene (HCFC-1232xf, bp. 57° C. to 58° C.) represented by $CF_2ClCCl=CH_2$ is that in which KOH is reacted with 1,1,2,3-tetrachloro-1-fluoropropane (HCFC-241db) or 1,2,3-trichloro-1,1-difluoropropane (HCFC-242dc) to remove hydrogen chloride (see Non-Patent Literature 1 and Non-Patent Literature 3, and Patent Literature 2). However, this method necessitates the problematic treatment of a large volume of waste and requires an improvement in the yield.

Patent Literature 3 discloses, as another related example, a process wherein 1,1,2,3-tetrachloropropene (HCC-1230xa, $CCl_2=CClCH_2Cl$) is fluorinated in a gas phase using a chromium-based catalyst. Patent Literature 4 also discloses a process for fluorinating 1,1,2,3-tetrachloropropene in a gas phase using a chromium-based catalyst. However, in these processes, fluorination advances too easily to result in a trifluorinated product, and it is extremely difficult to obtain a monofluorinated or difluorinated product.

Furthermore, Patent Literature 5 and Patent Literature 6 disclose that 1,1,2,3-tetrachloropropene (HCC-1230xa) represented by $CCl_2=CClCH_2Cl$, or 1,1,1,2,3-pentachloropropane (HCC-240db) represented by $CCl_3CHClCH_2Cl$ can be fluorinated by using halogenated antimony or a like catalyst in a liquid phase. However, if fluorination is conducted through these processes, a trifluorocarbon compound is mainly obtained, and it is extremely difficult to obtain a monofluorinated or difluorinated product.

As disclosed in Patent Literature 3 to 6, in the method wherein a chlorine-containing propane compound or a chlorine-containing propene compound is directly fluorinated, the trifluorination advances too easily and it is extremely difficult to stop the reaction at the monofluorolination or difluorolination stage.

CITATION LIST

Patent Literature

PTL 1: GB 772484
PTL 2: US 2787646
PTL 3: WO 2007/079431 A2
PTL 4: WO 2008/054781 A1
PTL 5: US 2009/0030247 A1
PTL 6: WO 2009/003157 A1

Non Patent Literature

NPL 1: *Inst. Heteroorg. Compds.* 1960, pp. 447-51
NPL 2: *Journal of the American Chemical Society*, 1947, 69, pp. 944-7
NPL 3: *Journal of the Chemical Society*, 1953, pp. 3371-8

SUMMARY OF INVENTION

Technical Problem

The present invention is made in view of the above-described conventional technical problems, and its main object is to provide an industrially applicable, simple and effective process for preparing a chlorine-containing propane or propene compound having 1 or 2 fluorine atoms.

Solution to Problem

The present inventors conducted extensive research to achieve the above object, and found the following. When at least one chlorine-containing compound selected from the group consisting of 1,1,1,2,3-pentachloropropane (HCC-240db), 1,1,2,3-tetrachloropropene (HCC-1230xa), and 2,3,3,3-tetrachloropropene (HCC-1230xf) is used as a starting material, and the starting material is brought into contact with anhydrous hydrogen fluoride while heating in the absence of a catalyst, a chlorine-containing propane or propene compound having 1 or 2 fluorine atoms can surprisingly be produced with high selectivity by a single-step reaction procedure. This solves the drawbacks of prior art methods, and efficiently produces chlorine-containing fluorocarbon compounds in an industrial scale. The present invention has been accomplished based on these findings.

More specifically, the present invention provides the following processes for preparing chlorine-containing fluorocarbon compounds.

1. A process for preparing at least one chlorine-containing fluorocarbon compound selected from the group consisting of chlorine-containing fluoropropane compounds represented by Formula (1): $CF_nCl_{3-n}CHClCH_2Cl$, wherein n is 1 or 2, and chlorine-containing fluoropropene compounds represented by Formula (2): $CF_nCl_{3-n}CCl=CH_2$, wherein n is 1 or 2, the process comprising the step of contacting at least one chlorine-containing compound selected from the group consisting of 1,1,1,2,3-pentachloropropane, 1,1,2,3-tetrachloropropene, and 2,3,3,3-tetrachloropropene with hydrogen fluoride in the absence of a catalyst while heating.

2. The process for preparing a chlorine-containing fluorocarbon compound according to Item 1, wherein the reaction product contains at least one compound selected from the group consisting of $CFCl_2CHClCH_2Cl$, $CF_2ClCHClCH_2Cl$, $CF_2ClCCl=CH_2$, and $CFCl_2CCl=CH_2$.

3. The process for preparing a chlorine-containing fluorocarbon compound according to Item 1, wherein at least one chlorine-containing compound selected from the group consisting of 1,1,1,2,3-pentachloropropane, 1,1,2,3-tetrachloropropene and 2,3,3,3-tetrachloropropene is contacted with hydrogen fluoride in a gas phase.

4. The process according to Item 3, wherein the reaction temperature is within the range of 200° C. to 350° C.

5. The process for preparing a chlorine-containing fluorocarbon compound according to Item 1, wherein at least one chlorine-containing compound selected from the group consisting of 1,1,1,2,3-pentachloropropane, 1,1,2,3-tetrachloropropene, and 2,3,3,3-tetrachloropropene is contacted with hydrogen fluoride in a liquid phase.

6. The process for preparing a chlorine-containing fluorocarbon compound according to Item 5, wherein the reaction temperature is within the range of 50° C. to 200° C.

The production process of the present invention is described below more specifically.

(1) Starting Compounds:

In the present invention, at least one chlorine-containing compound selected from the group consisting of 1,1,1,2,3-pentachloropropane (HCC-240db, bp. 179° C./760 mmHg, 51° C. to 53° C./3 mmHg) represented by Formula: $CCl_3CHClCH_2Cl$, 1,1,2,3-tetrachloropropene (HCC-1230xa, bp. 138° C.) represented by Formula: $CCl_2=CClCH_2Cl$, and 2,3,3,3-tetrachloropropene (HCC-1230xf, bp. 128° C.) represented by Formula: $CCl_3CCl=CH_2$ is used as the starting compound. These compounds are advantageous in that they are readily available at low cost. In the present invention, the starting compounds described above may be used singly or in combination.

(2) Reaction Process:

The preparation process of the present invention requires contacting the aforementioned starting compound with hydrogen fluoride in a gas or liquid phase in the absence of a catalyst while heating. This allows a reaction product to be obtained that contains at least one chlorine-containing compound selected from the group consisting of chlorine-containing fluoropropane compounds represented by Formula (1): $CF_nCl_{3-n}CHClCH_2Cl$, wherein n is 1 or 2, and a chlorine-containing fluoropropene compound represented by Formula (2): $CF_nCl_{3-n}CCl=CH_2$, wherein n is 1 or 2, at a high yield by a single-step reaction procedure.

Hereunder, specific conditions for the process of the present invention are explained for two cases: the case where the reaction is conducted in a gas phase, and the case where the reaction is conducted in a liquid phase.

(i) Reaction in a Gas Phase

The preparation process in a gas phase may be conducted by contacting the aforementioned starting compound with hydrogen fluoride in a gas phase in the absence of a catalyst. In this case, the starting compound may be in a liquid form when supplied, as long as the starting compound and hydrogen fluoride contact in a gas phase within the reaction temperature range descried below. For example, when the starting compound is liquid at an ordinary temperature and ordinary pressure, the starting compound is vaporized using a vaporizer (vaporization region), passed through the preheating region, and then supplied to the mixing region wherein the starting compound is contacted with anhydrous hydrogen fluoride; the reaction is thereby conducted in a gas phase. The reaction may also be carried out by supplying the starting compound in a liquid phase to a reactor, and evaporating the compound when the compound enters a reaction region to react with hydrogen fluoride. There is no limitation to the methods for evaporating the starting compound in the reaction region. The starting compound may be evaporated into a gas phase by, for example, filling a reaction tube with a material that exhibits excellent thermal conductivity, exerts no catalytic activity in the reaction of the present invention, and is stable to hydrogen fluoride, such as nickel beads, Hastelloy pellets, or the like, so as to homogenize the temperature distribution within the reaction tube, heating the reaction tube to not less than the evaporation temperature of the starting compound, and supplying the starting compound in a liquid phase thereinto.

Hydrogen fluoride may generally be supplied to a reactor in a gas phase together with a starting compound. The amount of the hydrogen fluoride supplied is generally not less than about 2 mol, preferably within the range of about 5 to 100 mol, and more preferably within the range of about 5 to 20 mol, per mol of the aforementioned starting compound. By setting the amount of starting compound within such a range, the selectivity of at least one compound selected from the group consisting of chlorine-containing fluoropropane compounds represented by Formula (1): $CF_nCl_{3-n}CHClCH_2Cl$, and chlorine-containing fluoropropene compounds represented by Formula (2): $CF_nCl_{3-n}CCl=CH_2$ can be maintained in a desirable range.

The aforementioned starting compound may be supplied to the reactor as is, or may be diluted with an inert gas such as nitrogen, helium, or argon and then supplied to the reactor. The form of the reactor used in the gas phase reaction is not particularly limited. Examples of usable reactors include a hollow adiabatic reactor, an adiabatic reactor packed with a porous or nonporous metal or medium that improves the gas-phase mixing state between hydrogen fluoride and the starting compound. Also usable is a multitubular reactor in which a heat transmitting medium is used to cool the reactor and to homogenize the temperature distribution within the reactor. It is preferable that the reactor be formed of a material that is resistant to the corrosive action of hydrogen fluoride, such as HASTELLOY®, INCONEL®, MONEL®, and INCOLLOY®.

The reaction temperature in the gas phase reaction, i.e., the temperature in the reactor, is preferably about 200° C. to 350° C., and more preferably about 200° C. to 300° C. If the reaction temperature is higher than this range, the selectivity of the target product undesirably decreases. Conversely, if the reaction temperature is lower than this range, the starting compound conversion rate undesirably decreases.

The pressure during the reaction is not particularly limited, as long as the starting compound and hydrogen fluoride are present in the form of a gas phase, and the reaction may be conducted under ordinary pressure, reduced pressure or increased pressure. More specifically, the reaction in a gas phase may be conducted under a reduced pressure, at atmospheric pressure (0.1 MPa), or under an increased pressure to the extent that the starting material does turn into a liquid state.

The reaction time is not particularly limited. However, the contact time, which is determined by V/Fo, may be adjusted to a range of about 0.1 to 100 sec, and preferably about 1 to 30 sec. V/Fo is the ratio of the reaction volume V (cc) in a gas phase to the total flow rate $F_o$ (flow rate at 0° C., 0.1 MPa: cc/sec) of the starting material gases (starting compound, hydrogen fluoride and inert gas) supplied to the reaction system.

Under the above reaction conditions, a reaction product that contains at least one chlorine-containing compound selected from the group consisting of chlorine-containing fluoropropane compounds represented by Formula (1): $CF_nCl_{3-n}CHClCH_2Cl$, wherein n is 1 or 2, and chlorine-containing fluoropropene compounds represented by Formula (2): $CF_nCl_{3-n}CCl=CH_2$, wherein n is 1 or 2, can be obtained at the reactor outlet. The resulting reaction products may be collected after being purified by distillation, etc. The collected product may be used for a desired purpose as is, or may be converted into another compound.

(ii) Reaction in a Liquid Phase

The reaction in a liquid phase can be conducted by contacting the aforementioned starting material, i.e., at least one chlorine-containing compound selected from the group consisting of 1,1,1,2,3-pentachloropropane, 1,1,2,3-tetrachloropropene, and 2,3,3,3-tetrachloropropene, with hydrogen fluoride in a liquid form in the absence of a catalyst.

The molar ratio of hydrogen fluoride to the chlorine-containing compound that serves as the starting material (HF/starting compound) is preferably about 2 to 100, and more preferably about 5 to 50.

The reaction temperature is preferably about 50° C. to 200° C., and more preferably about 80° C. to 150° C.

The reaction pressure is preferably about 0.25 to 5.0 MPa, and more preferably about 0.5 to 3.0 MPa. The specific pressure may be selected depending on the type of starting material used, the reaction temperature, etc., so that the chlorine-containing compound and hydrogen fluoride are present in a liquid form.

The reaction time is generally about 0.5 to 72 hours, and preferably about 1 to 48 hours.

(3) Reaction Product

The present invention provides a reaction product that contains at least one compound selected from the group consisting of chlorine-containing fluoropropane compounds represented by Formula (1): $CF_nCl_{3-n}CHClCH_2Cl$, wherein n is 1 or 2, and chlorine-containing fluoropropene compounds represented by Formula (2): $CF_nCl_{3-n}CCl=CH_2$, wherein n is 1 or 2.

Examples of the chlorine-containing fluoropropane compounds represented by Formula (1): $CF_nCl_{3-n}CHClCH_2Cl$, wherein n is 1 or 2, include $CFCl_2CHClCH_2Cl$ (HCFC-241db), $CF_2ClCHClCH_2Cl$ (HCFC-242dc), etc. Examples of the chlorine-containing fluoropropene compounds represented by Formula (2): $CF_nCl_{3-n}CCl=CH_2$, wherein n is 1 or 2, include $CF_2ClCCl=CH_2$ (HCFC-1232xf), $CFCl_2CCl=CH_2$ (HCFC-1231xf), etc. In addition to these fluorine-containing compounds, compounds such as $CCl_2=CClCH_2Cl$ (HCC-1230xa) may be also included in the reaction products obtained by the process of the present invention.

Because the starting material and each reaction product have greatly different boiling points, they can be easily separated by distillation, etc.

In the present invention, when the reaction is conducted in a gas phase, the proportion of the fluoropropene compound represented by Formula (2) increases, and when the reaction is conducted in a liquid phase, the proportion of the fluoropropane compound represented by Formula (1) increases. Therefore, the proportions of the compounds contained in the reaction product can be suitably controlled by selecting the specific production conditions depending on the type of targeted reaction product.

When the conversion rate of the starting material is unduly low, the starting material can be recycled by returning it to the reactor after isolation and collection of the target product. Compounds in which the fluorination did not advance to the desired level (i.e., a precursor of the intended product) can also be recycled by being returned to the reactor, thereby maintaining high productivity.

Advantageous Effects of Invention

The present invention uses the aforementioned chlorine-containing compounds as a starting material, and allows obtaining at least one compound selected from the group consisting of specific chlorine-containing fluoropropane compounds and chlorine-containing fluoropropene compounds having 1 or 2 fluorine atoms at a high yield for a relatively short reaction time by a single-step reaction procedure. Therefore, the process of the present invention is industrially advantageous for the production of chlorine-containing fluoropropane compounds and fluoropropene compounds.

BRIEF DESCRIPTION OF DRAWING

FIG. 1 is a schematic diagram, showing the reactor used in Example 1.

DESCRIPTION OF EMBODIMENTS

The present invention is described in more detail below, with reference to Production Examples of 1,1,1,2,3-pentachloropropane (HCC-240db), 1,1,2,3-tetrachloropropene (HCC-1230xa), and 2,3,3,3-tetrachloropropene (HCC-1230xf) that serve as starting materials, and the Examples of the present invention.

Production Example 1

1,1,1,2,3-Pentachloropropane (HCC-240db) was produced by sequentially conducting Steps (1) to (3) described below.

(1) Process for Preparing 1,1,1,3-Tetrachloropropane (HCC-250fb)

A 1,000 ml autoclave equipped with a thermometer, a vacuum line, a nitrogen purge line, a feeding line, a gauge, and a pressure relief valve was charged with 9.72 g (171 mmol) of soft iron powder, 48 g (260 mmol) of triethyl phosphate, 200 mg of ferric chloride, and 810 g (5.26 mol) of carbon tetrachloride, and was purged 5 times with nitrogen, and once with ethylene. The autoclave was then evacuated and charged, under stirring, with ethylene to a gauge pressure of 0.4 MPa. When the autoclave was heated to an internal temperature of 110° C., the reaction was initiated, and the internal temperature was increased to 134° C., while the pressure was decreased from 0.8 MPa to 0.25 MPa. While the pressure of ethylene was maintained at 0.8 MPa, stirring was continued at an internal temperature of 120° C. for 9 hours. Then, 24 g (130 mmol) of triethyl phosphate was injected into the autoclave, and the reaction was further allowed to proceed at 120° C. for 7 hours.

After completion of the reaction, the crude product was analyzed by gas chromatography. The results of the analysis confirmed that carbon tetrachloride was completely consumed. The crude product was washed twice with a threefold amount of water, and the organic layer was dried over magnesium sulfate to obtain HCC-250fb with a purity of 79.8%, as determined by gas chromatography. The by-product generated was an oligomer in which hydrogen chloride was added to ethylene.

The obtained crude product was distilled under reduced pressure (10 mmHg), and a fraction at 70° C. to 74° C. was collected to obtain 814 g (4.94 mol, yield 91%) of HCC-250fb with a purity of 98% or more.

(2) Process for Preparing 1,1,3-Trichloropropene (HCC-1240za) and 3,3,3-trichloropropene (HCC-1240zf)

A 1,000 ml four-necked flask equipped with a thermometer and a condenser tube was charged with 540 g (3.0 mol) of HCC-250fb obtained in Step (1) above, 630 g of 40% aqueous KOH solution, and 10 g of phase-transfer catalyst (Aliquat 336). The reaction was allowed to proceed under stirring at 80° C. in an oil bath for 3 hours. After completion of the reaction, the resulting product was cooled and distilled under reduced pressure (10 to 20 mmHg), and a fraction at 67.7° C. to 81.9° C. was collected to obtain 390 g of a mixture of HCC-1240zf and HCC-1240za (HCC-1240zf:HCC-1240za=62:38 (2.68 mol, yield: 89.3%)).

(3) Process for Preparing 1,1,1,2,3-Pentachloropropane (HCC-240db)

A 500 ml flask equipped with a high-pressure mercury vapor lamp, a magnetic stirrer and two gas ports was charged with 265 g of the mixture of the 1,1,3-trichloropropene (HCC-1240za) and 3,3,3-trichloropropene (HCC-1240zf) obtained in Step (2) above, followed by cooling to 0° C. in an ice bath. The content was stirred under irradiation with ultraviolet light, and chlorine gas was introduced at 20 to 120 mL/min from one of the gas ports to the area above the liquid surface of the content. The reaction mixture was intermittently sampled, and analyzed by gas chromatography to measure the degree of chlorination. After three hours, the trichloropropene was entirely consumed, and 370 g of product was obtained. The obtained product was distilled under reduced pressure (3 mmHg), and a fraction at 51° C. to 53° C. was collected to obtain 330 g of 1,1,1,2,3-pentachloropropane (HCC-240db) at a purity of 99.6%.

Production Example 2

The following process was performed to prepare a mixture of 1,1,2,3-tetrachloropropene (HCC-1230xa) and 2,3,3,3-tetrachloropropene (HCC-1230xf).

Process for Preparing 1,1,2,3-Tetrachloropropene (HCC-1230xa) and 2,3,3,3-Tetrachloropropene (HCC-1230xf)

A 1,000 ml four-necked flask equipped with a thermometer and a condenser tube was charged with 330 g (1.52 mol) of 1,1,1,2,3-pentachloropropane (HCC-240db) obtained in Step (3) of Production Example 1, 310 g of 40% aqueous KOH solution, and 6 g of phase-transfer catalyst (Aliquat 336).

The reaction was allowed to proceed under stirring at 80° C. in an oil bath for 3 hours. After completion of the reaction, the resulting product was cooled and distilled under reduced pressure (1 mmHg), and a fraction at 20° C. to 22° C. was collected to obtain 259 g (1.44 mol, yield 94.8%) of a mixture of HCC-1230xa and HCC-1230xf (HCC-1230xa:HCC-1230xf=38:62 (1.44 mol, yield: 94.8%)) at a purity of 99.9%.

Example 1

A tubular reactor made of HASTELLOY®, having an inner diameter of 10 mm and a length of 82 cm was packed with 33.0 g of nickel beads (cylinder shaped, diameter: 2 mm; height: 2 mm) that were inactive against the reaction. The length of the packed nickel beads was 8.2 cm, and the void volume of this packed bed of the nickel beads was 2.3 cm$^3$. An insertion tube was introduced inside the reaction tube from the top to measure the temperature inside the reaction tube including the nickel bead-packed bed. FIG. 1 schematically illustrates the reactor used. The reaction tube was maintained at atmospheric pressure (0.1 MPa) and a temperature of 290° C., and anhydrous hydrogen fluoride (HF) was continuously introduced into the reactor at 60 cc/min (flow rate at 0° C. and 0.1 MPa) for 0.5 hours.

Thereafter, 1,1,1,2,3-pentachloropropane (HCC-240db, purity: 99.6%) was continuously supplied at a rate of 6.0 cc/min (flow rate at 0° C. and 0.1 MPa) while 1,1,1,2,3-pentachloropropane was added dropwise in a liquid phase from the upper portion of the reaction tube, and the internal temperature of the nickel bead-packed bed was maintained at 290° C. to initiate the reaction. In this process, the temperature of the nickel bead-packed bed greatly exceeds the boiling point of 1,1,1,2,3-pentachloropropane (179° C./760 mmHg); thus, the 1,1,1,2,3-pentachloropropane is in a gas phase when passing through the nickel bead-packed bed.

During the reaction, nitrogen ($N_2$) was supplied at 50 cc/min (flow rate at 0° C. and 0.1 MPa) from the outlet side of the reactor, and was collected together with the reaction product. The internal temperature of the nickel bead-packed bed was measured at three points at equal intervals between the inlet side and the outlet side of the reaction tube; thereby, the average temperature was determined as a reaction temperature. The molar ratio of HF to 1,1,1,2,3-pentachloropropane (HF/1,1,1,2,3-pentachloropropane) was 10. The contact (residence) time ($V/F_0$) was calculated as 2.1 sec, based on the void volume (V) of the nickel bead-packed bed and the total flow rate ($F_0$) of the reactant. The internal temperature of the reaction tube at the point 5 cm above the upper surface of the nickel bead-packed bed was about 264° C., and the internal temperature at the point 15 cm below the bottom surface of the packed bed was about 244° C. Therefore, the void volume of about 15 cm$^3$, which is the volume corresponding to a length of 20 cm in which the nickel beads are not packed, was also considered to be included in the reaction region in addition to that of the nickel bead-packed bed. Based on this, the contact (residence) time ($V/F_0$) was recalculated. As a result, $V/F_0$ was 15.7 sec. The contact (residence) time ($V/F_0$) was calculated in the same manner as above in the other Examples.

The outflow from the reactor obtained 3 hours after the initiation of the reaction was analyzed by gas chromatography. Among the reaction products, high-boiling products having a boiling point of 50° C. or more were quantified in the manner described below. Specifically, HCFC-141b in which a predetermined amount of perchloroethylene had been dissolved as an internal standard substance was mixed with ice water to preliminarily subject it to liquid separation. The component obtained at the outlet of the reactor was bubbled in the HCFC-141b layer for a predetermined period of time so that an organic substance was extracted in the HCFC-141b layer, and the acid content of hydrogen fluoride and hydrogen chloride was dissolved in the ice water layer.

The extraction liquid was heated to 20° C., and the HCFC-141b layer was analyzed by gas chromatography (FID). As a column, a DB-1 (60 m) capillary column was used. The amount of each product produced was converted into a molar ratio, by comparing the detected area of each of the obtained products with that of the perchloroethylene, which served as the internal standard substance, with taking coefficient for gas chromatography into consideration.

Comparatively, low-boiling products having a boiling point of 50° C. or less were quantified in the manner described below. Specifically, two washing columns filled with water were connected in series and connected to the reactor outlet, and then immersed in a water bath to be preliminarily heated to 60° C. Thereafter, the reactor outflow was introduced into the washing columns to perform bubbling so as to wash the acid content. Then, the gas component, which had been dewatered through a CaCl$_2$ tube, was collected and analyzed by gas chromatography (FID). At this time, a predetermined amount of HFC-32 as an internal standard substance was introduced from the reactor outlet side, together with the reactor outflow, to the washing columns. As a column, a GS-GASPRO (60 m) capillary column was used. The amount of each product produced was converted into a molar ratio, by comparing the detected area of each of the obtained products with that of the HFC-32, which served as the internal standard substance, with taking coefficient for gas chromatography into consideration. In the manner described above, the components from the reactor outlet were quantified. Table 1 shows the result.

The products obtained in this Example are shown below.
CCl$_2$=CClCH$_2$Cl (HCC-1230xa)
CFCl$_2$CHClCH$_2$Cl (HCFC-241db)
CFCl$_2$CCl=CH$_2$ (HCFC-1231xf)
CF$_2$ClCHClCH$_2$Cl (HCFC-242dc)
CF$_2$ClCCl=CH$_2$ (HCFC-1232xf)
CF$_3$CH=CH$_2$ (HFC-1243zf)

Example 2

The reaction was performed under the same conditions as in Example 1, except that the reaction temperature was changed to 265° C. Table 1 shows the results of the analysis with respect to the product obtained 3 hours after the initiation of the reaction.

Example 3

The reaction was performed under the same conditions as in Example 1, except for using, as a filler packed into the reaction tube, 16.5 g of Hastelloy pellets (thickness: 1 mm; length: 3 mm; width: 3 mm) made of the same material as that of the reaction tube was used in place of the nickel beads. The length of the Hastelloy pellet-packed bed was 14.6 cm, and the void volume in this packed bed was 4.0 cm$^3$; thus, V/F$_0$ was calculated as 17.3 sec. Table 1 shows the results of the analysis with respect to the product obtained 3 hours after the initiation of the reaction.

Example 4

The reaction was performed under the same conditions as in Example 1, except that the starting material used was changed to a mixture of 1,1,2,3-tetrachloropropene (HCC-1230xa) and 2,3,3,3-tetrachloropropene (HCC-1230xf) (HCC-1230xa:HCC-1230xf=38:62, purity: 99.9%), and 49.5 g of nickel beads were charged. The void volume in this packed bed was 3.5 cm$^3$; thus, V/F$_0$ was calculated as 16.8 sec. Table 1 shows the results of the analysis with respect to the product obtained 3 hours after the initiation of the reaction.

TABLE 1

|  | Ex. 1 | Ex. 2 | Ex. 3 | Ex. 4 |
|---|---|---|---|---|
| Reaction Temperature (° C.) | 290 | 265 | 290 | 290 |
| Molar Ratio | 10 | 10 | 10 | 10 |
| V/F$_0$ (sec.) | 15.7 | 15.7 | 17.3 | 16.8 |
| Time passed after the initiation of the reaction (h) | 3 | 3 | 3 | 3 |
| Conversion Rate of the Starting Material (%) | 55.1 | 27.3 | 45.0 | 62.4 |
| Product Selectivity (%) |  |  |  |  |
| HCC-1230xa | 14.8 | 31.9 | 18.2 | 16.9 |
| HCFC-241db | 10.3 | 8.5 | 10.3 | 7.8 |
| HCFC-1231xf | 5.2 | 7.7 | 4.8 | 6.1 |
| HCFC-242dc | 1.3 | 0.9 | 1.6 | 1.8 |
| HCFC-1232xf | 61.9 | 47.4 | 58.0 | 59.0 |
| HFC-1243zf | 0.2 | 0.1 | 0.1 | 0.1 |
| Others | 6.3 | 3.5 | 7.0 | 8.3 |

Example 5

A 100 mL autoclave made of HASTELLOY® that was equipped with a thermometer, a vacuum line, a purge line, a nitrogen line, a feeding line, stirring blades, and a gauge was charged with 10.0 g (46 mmol) of 1,1,1,2,3-pentachloropropane (HCC-240db, purity: 99.6%).

After closing, the autoclave was cooled to an internal temperature of −40° C. in a dry-ice/acetone bath. Thereafter, the internal pressure of the autoclave was reduced, and then 18.4 g (920 mmol) of anhydrous hydrogen fluoride was introduced thereinto. The autoclave was heated to an internal temperature of 130° C. over 2 hours, followed by stirring at 130° C. for 5 hours. The gauge pressure in the autoclave increased to the range of 2.0 MPa to 2.2 MPa. When the autoclave was cooled to an internal temperature of to 14° C., the pressure became 0.5 MPa. After removing the hydrogen chloride (HCl) that was generated by releasing the pressure, the pressure was adjusted to 0 MPa, followed by further heating at 130° C. for 30 hours. During the heating, the pressure was released twice in the same manner as described above.

After completing the reaction, the temperature was increased to 50° C., and hydrogen chloride and hydrogen fluoride were removed by being passed through a scrubber, and the gas phase was passed through a calcium chloride column and then collected. The amount of the collected gas phase was 0.3 g.

The liquid phase was washed with water twice, obtaining 6.2 g of crude product. The gas phase and the liquid phase were analyzed by gas chromatography. The analytic results show that the contents of the components in the liquid phase and the gas phase were as follows. The components in the liquid phase were 9.5% HCFC-242dc, 1.2% HCFC-241db, and 89.1% HCC-240db; and the components in the gas phase were 1.3% HCFC-1232xf, 1.1% CF$_3$CCl=CH$_2$ (HCFC-1233xf), and 95.8% CF$_3$CH=CH$_2$ (HFC-1243zf).

Example 6

A 100 mL autoclave made of HASTELLOY® that was equipped with a thermometer, a vacuum line, a purge line, a nitrogen line, a feeding line, stirring blades, and a gauge was charged with 10.0 g (46 mmol) of 1,1,1,2,3-pentachloropropane (HCC-240db, purity: 99.6%).

After closing, the autoclave was cooled to an internal temperature of 0° C. by ice water. Thereafter, the internal pressure of the autoclave was reduced, and then 18.4 g (920 mmol) of anhydrous hydrogen fluoride was introduced thereinto. The autoclave was heated to an internal temperature of 110° C. over 2 hours, followed by stirring at 110° C. for 15 hours. The gauge pressure in the autoclave increased to the range of 1.1 MPa to 1.2 MPa. When the autoclave was cooled to an internal temperature of 5° C., the pressure became 0.2 MPa. After removing the hydrogen chloride (HCl) that was generated by releasing the pressure, the pressure was adjusted to 0 MPa, followed by further heating at 110° C. for 10 hours. During the heating, the pressure was released twice in the same manner as described above.

After completing the reaction, the temperature was increased to 50° C., and hydrogen chloride and hydrogen fluoride were removed by being passed through a scrubber. The reaction liquid was washed with water twice, obtaining 9.4 g of crude product (organic layer). The crude product was analyzed by gas chromatography. The analytic results show that the contents of the components in the crude product was 7.1% HCFC-241db, 0.1% HCFC-1231xf, and 92.6% HCC-240db.

The invention claimed is:

1. A process for preparing at least one chlorine-containing fluorocarbon compound selected from the group consisting of chlorine-containing fluoropropane compounds represented by Formula (1): $CF_nCl_{3-n}CHClCH_2Cl$, wherein n is 1 or 2, and chlorine-containing fluoropropene compounds represented by Formula (2): $CF_nCl_{3-n}CCl\!=\!CH_2$, wherein n is 1 or 2, the process comprising the step of contacting at least one chlorine-containing compound as a starting material selected from the group consisting of 1,1,1,2,3-pentachloropropane, 1,1,2,3-tetrachloropropene, and 2,3,3,3-tetrachloropropene with hydrogen fluoride in the absence of a catalyst while heating, wherein the molar ratio of hydrogen fluoride to the chlorine-containing compound that serves as the starting material is 2 to 100, and wherein at least one chlorine-containing compound is contacted with the hydrogen fluoride in a liquid phase.

2. The process for preparing a chlorine-containing fluorocarbon compound according to claim 1, wherein the reaction product contains at least one compound selected from the group consisting of $CFCl_2CHClCH_2Cl$, $CF_2ClCHClCH_2Cl$, $CF_2ClCCl\!=\!CH_2$, and $CFCl_2CCl\!=\!CH_2$.

3. The process for preparing a chlorine-containing fluorocarbon compound according to claim 1, wherein the reaction temperature is within the range of 50° C. to 200° C.

* * * * *